(12) United States Patent
Lee (10) Patent No.: US 8,718,780 B2
(45) Date of Patent: May 6, 2014

(54) SYSTEM FOR SELECTIVELY PERFORMING LOCAL AND RADIAL PERIPHERAL STIMULATION

(75) Inventor: Dongchul Lee, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 131 days.

(21) Appl. No.: 13/197,949

(22) Filed: Aug. 4, 2011

(65) Prior Publication Data

US 2012/0041511 A1 Feb. 16, 2012

Related U.S. Application Data

(60) Provisional application No. 61/373,692, filed on Aug. 13, 2010.

(51) Int. Cl.
*A61N 1/18* (2006.01)

(52) U.S. Cl.
USPC .............................................. 607/46; 607/2

(58) Field of Classification Search
USPC ....................................... 607/46, 2
See application file for complete search history.

(56) References Cited

U.S. PATENT DOCUMENTS

| | | | |
|---|---|---|---|
| 6,405,082 B1 * | 6/2002 | Borgenicht | 607/5 |
| 6,516,227 B1 | 2/2003 | Meadows et al. | |
| 6,895,280 B2 | 5/2005 | Meadows et al. | |
| 7,539,538 B2 | 5/2009 | Parramon et al. | |
| 7,920,915 B2 | 4/2011 | Mann et al. | |
| 2003/0139781 A1 | 7/2003 | Bradley et al. | |
| 2004/0015205 A1 | 1/2004 | Whitehurst et al. | |
| 2005/0267546 A1 | 12/2005 | Parramon et al. | |
| 2007/0073356 A1 * | 3/2007 | Rooney et al. | 607/46 |
| 2007/0112404 A1 | 5/2007 | Mann et al. | |
| 2010/0010566 A1 | 1/2010 | Thacker et al. | |
| 2010/0121409 A1 | 5/2010 | Kothandaraman et al. | |

* cited by examiner

*Primary Examiner* — Joseph Stoklosa
(74) *Attorney, Agent, or Firm* — Vista IP Law Group LLP (57) ABSTRACT

A control system for use with a neurostimulator comprises a user interface for receiving an input from a user and a controller. The user interface has a first control and a second control. The controller is configured for, in response to actuating the first control, operating the neurostimulation control system in a PNFS programming mode, and for, in response to actuating the second control, operating the neurostimulation control system in a PNS programming mode. A method of providing therapy to a patient comprises initially conveying pulsed electrical current at a pulse width into a peripheral tissue region of the patient to create a side effect via stimulation of one of a nerve ending and neural axon, and subsequently conveying pulsed electrical current at an adjusted pulse width into the peripheral tissue region to create a therapeutic effect via stimulation of the other one of the nerve ending and neural axon.

20 Claims, 8 Drawing Sheets

SYSTEM FOR SELECTIVELY PERFORMING LOCAL AND RADIAL PERIPHERAL STIMULATION

RELATED APPLICATION DATA

The present application claims the benefit under 35 U.S.C. §119 to U.S. provisional patent application Ser. No. 61/373,692, filed Aug. 13, 2010. The foregoing application is hereby incorporated by reference into the present application in its entirety.

FIELD OF THE INVENTION

The present invention relates to tissue stimulation systems, and more particularly, to a system and method for peripherally stimulating nerve tissue.

BACKGROUND OF THE INVENTION

Implantable neurostimulation systems have proven therapeutic in a wide variety of diseases and disorders. In recent investigations, Peripheral Stimulation (PS) (i.e., stimulation of nerve tissue outside of the spinal cord and brain), which includes Peripheral Nerve Field Stimulation (PNFS) techniques that stimulate nerve tissue directly at the symptomatic site of the disease or disorder (e.g., at the source of pain), and Peripheral Nerve Stimulation (PNS) techniques that directly stimulate bundles of peripheral nerves that may not necessarily be at the symptomatic site of the disease or disorder, has demonstrated efficacy in the treatment of chronic pain syndromes (e.g., painful peripheral neuropathy (PN), post-herpetic neuralgia (PHN), fibromyalgia syndrome (FMS), failed back surgery syndrome (FBSS), Arachnoiditis, occipital neuralgia, peripheral pelvic pain, cardiac pain, etc.) and incontinence, and a number of additional applications are currently under investigation.

An implantable neurostimulation system, whether used in the context of PS or another stimulation application, typically includes one or more electrode carrying stimulation leads, which are implanted at the desired stimulation site. In PS, the stimulation lead(s) are implanted in the subcutaneous tissues of a peripheral region, such as the lower back region, cervical region, arm, or leg. The implantable neurostimulation system further includes a neurostimulator (e.g., an implantable pulse generator (IPG)) implanted within a tissue pocket remotely from the stimulation site, but coupled to the stimulation lead(s). Thus, electrical pulses can be delivered from the neurostimulator to the stimulation lead(s) to stimulate or activate a volume of neural tissue. In particular, electrical energy conveyed between at least one cathodic electrode and at least one anodic electrodes creates an electrical field, which when strong enough, depolarizes (or "stimulates") the neurons beyond a threshold level, thereby inducing the firing of action potentials (APs) that propagate along the neural fibers.

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the magnitude, duration, and rate of the current pulses. The stimulation regimen will typically be one that provides stimulation energy to all of the target tissue that must be stimulated in order to provide the therapeutic benefit, yet minimizes the volume of non-target tissue that is stimulated. In the case of PS, such a therapeutic benefit is accompanied by "paresthesia," i.e., a tingling sensation that is effected by the electrical stimuli applied through the electrodes.

While PS has been generally useful in treating patients, there still remain issues. For example, an electrical field applied to a particular peripheral region may not only stimulate nerve endings that innervate a region local to the applied electrical field, but also stimulate neural axons that innervate tissue remote from the applied electrical field. As such, it is often difficult to selectively perform PNFS and PNS. That is, when PNFS is desired, PNS may inadvertently be performed instead of or in addition to PNS, and when PNS is desired, PNFS may inadvertently be performed instead of or in addition to PNS.

There, thus, remains a need for an improved technique to selectively perform PNFS and PNS in a patient.

SUMMARY OF THE INVENTION

In accordance with one aspect of the present inventions, a neurostimulation control system for use with a neurostimulator is provided. The neurostimulation system comprises a user interface configured for receiving an input from a user. The interface has a first control and a second control, each of which may be, e.g., a graphical icon. The neurostimulation control system further comprises a controller configured for, in response to a single actuation of the first control, operating the neurostimulation control system in a peripheral nerve field stimulation (PNFS) programming mode, and for, in response to a single actuation of the second control, operating the neurostimulation control system in a peripheral nerve stimulation (PNS) programming mode. The user interface and controller may be contained within an external control device.

In one embodiment, the controller, when the neurostimulation control system is in the PNFS mode, is configured for only allowing a user to program the neurostimulator to convey pulsed anodic stimulation current at a pulse width below an upper limit (e.g., less than 700 µs), and when the neurostimulation control system is in the PNS mode, is configured for only allowing a user to program the neurostimulator to convey pulsed cathodic stimulation current at a pulse width above a lower limit (e.g., greater than 500 µs).

In another embodiment, the controller, when the neurostimulation control system is in the PNFS mode, is configured for automatically programming the neurostimulator to convey pulsed anodic stimulation current at a first pulse width (e.g., a value less than 700 µs), and when the neurostimulation control system is in the PNS mode, is configured for automatically programming the neurostimulation to convey pulsed cathodic stimulation current at a second pulse width (e.g., a value greater than 500 µs).

In accordance with another aspect of the present inventions, a method of providing therapy (e.g., a reduction in or elimination of pain) to a patient is provided. The method comprises initially conveying pulsed electrical current at a pulse amplitude and a pulse width into a peripheral tissue region of the patient, whereby one of a nerve ending is stimulated to create a side effect local to the peripheral neural tissue region and a neural axon is stimulated to create a side effect remote from the peripheral neural tissue region. The method further comprises adjusting the pulse width, and subsequently conveying pulsed electrical current at the adjusted pulse width into the peripheral tissue region of the patient, whereby only one of the other of the nerve ending is stimulated to create a therapeutic effect local to the peripheral neural tissue region and the neural axon is stimulated to create a therapeutic effect remote from the peripheral neural tissue region. In one method, both the initially and subsequently conveyed pulsed electrical current have the same pulse amplitude. Another method further comprises adjusting the pulse amplitude, wherein the pulsed electrical current is subsequently conveyed at the adjusted pulse amplitude into the peripheral region of the patient.

If the nerve ending is stimulated to create the side effect, and the neural axon is stimulated to create the therapeutic effect, the subsequently conveyed pulsed electrical current is preferably cathodic. In this case, the pulse width may be adjusted by increasing the pulse width (e.g., to a value greater than 500 μs), and if the initially conveyed pulsed electrical current is anodic, the polarity of the pulsed electrical current is switched from anodic to cathodic. If the neural axon is stimulated to create the side effect, and the nerve ending is stimulated to create the therapeutic effect, the subsequently conveyed pulsed electrical current is preferably anodic. In this case, the pulse width may be adjusted by decreasing the pulse width (e.g., to a value less than 700 μs), and if the initially conveyed pulsed electrical current is cathodic, the polarity of the pulsed electrical current is switched from cathodic to anodic.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 9a is a diagram of strength-duration curves for the stimulation of nerve endings and neural axons generated from the bar graph of FIG. 8a.

DETAILED DESCRIPTION OF THE EMBODIMENTS

Figure 1:
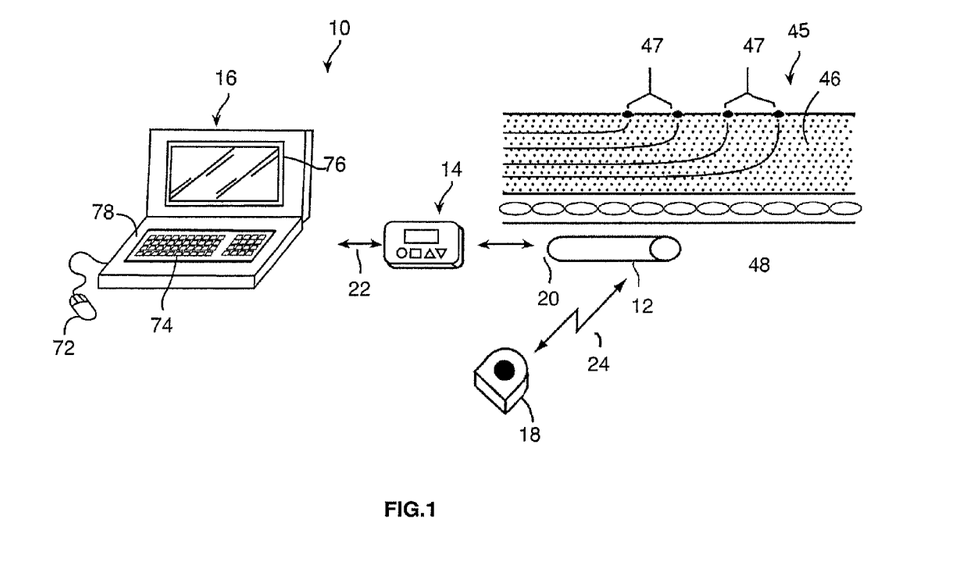
FIG. 1 is plan view of one embodiment of a peripheral tissue stimulation system arranged in accordance with the present inventions.

Turning first to FIG. 1, an exemplary neurostimulation system 10 is used to selectively perform Peripheral Nerve Field Stimulation (PNFS) and Peripheral Nerve Stimulation (PNS). The system 10 generally includes a neurostimulator in the form of a microstimulator 12, external control devices, and in particular a handheld remote controller (RC) 14 and a clinician's programmer (CP) 16, and an external charger 18.

The microstimulator 12 includes pulse generation circuitry that delivers electrical stimulation energy in the form of a pulsed electrical waveform (i.e., a temporal series of electrical pulses) to tissue in which the microstimulator 12 is implanted in accordance with a set of stimulation parameters. As shown in FIG. 1, the microstimulator 12 is subcutaneously implanted within a peripheral region 45 (e.g., an arm, leg, lower back, neck, etc.) of a patient using suitable means, such as a needle. The preferred placement of the microstimulator 12 is just below the cutaneous layer 46 of the patient. As there shown, the microstimulator 12 is located adjacent one or more nerve endings 47 that provide sensory information local to the peripheral region 44 and one or more neural axons 48 that provide afferent or efferent information to or from a region remote from the peripheral region 44.

The RC 14 may be used to telemetrically control the microstimulator 12 via a bi-directional RF communications link 20. Such control allows the microstimulator 12 to be turned on or off and to be programmed with different stimulation parameters. The microstimulator 12 may also be operated to modify the programmed stimulation parameters to actively control the characteristics of the electrical stimulation energy output by the microstimulator 12.

The CP 16 provides clinician detailed stimulation parameters for programming the microstimulator 12 in the operating room and in follow-up sessions. The CP 16 may perform this function by indirectly communicating with the microstimulator 12 through the RC 14 via an IR communications link 22. Alternatively, the CP 16 may directly communicate with the microstimulator 12 via an RF communications link (not shown). The clinician detailed stimulation parameters provided by the CP 16 are also used to program the RC 14, so that the stimulation parameters can be subsequently modified by operation of the RC 14 in a stand-alone mode (i.e., without the assistance of the CP 16).

The external charger 18 is a portable device used to transcutaneously charge the microstimulator 12 via an inductive link 24. For purposes of brevity, the details of the external charger 18 will not be described herein. Details of exemplary embodiments of external chargers are disclosed in U.S. Pat. No. 6,895,280, which has been previously incorporated herein by reference. Once the microstimulator 12 has been programmed, and its power source has been charged by the external charger 18 or otherwise replenished, the microstimulator 12 may function as programmed without the RC 14 or CP 16 being present.

Figure 2:
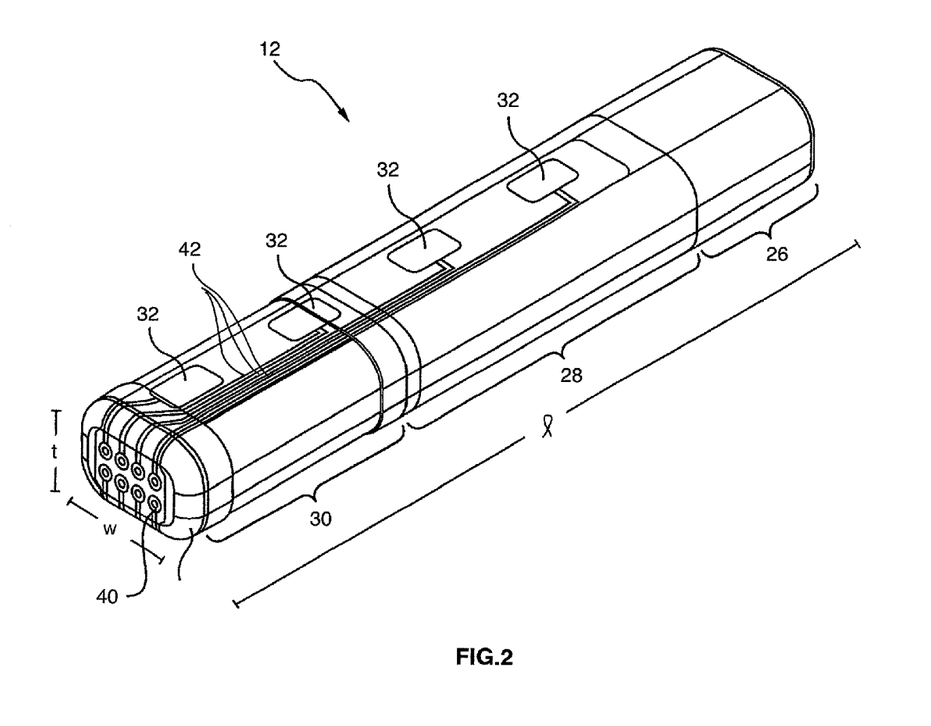
FIG. 2 is a perspective view of a microstimulator used in the peripheral stimulation system of FIG. 1.
Figure 3:
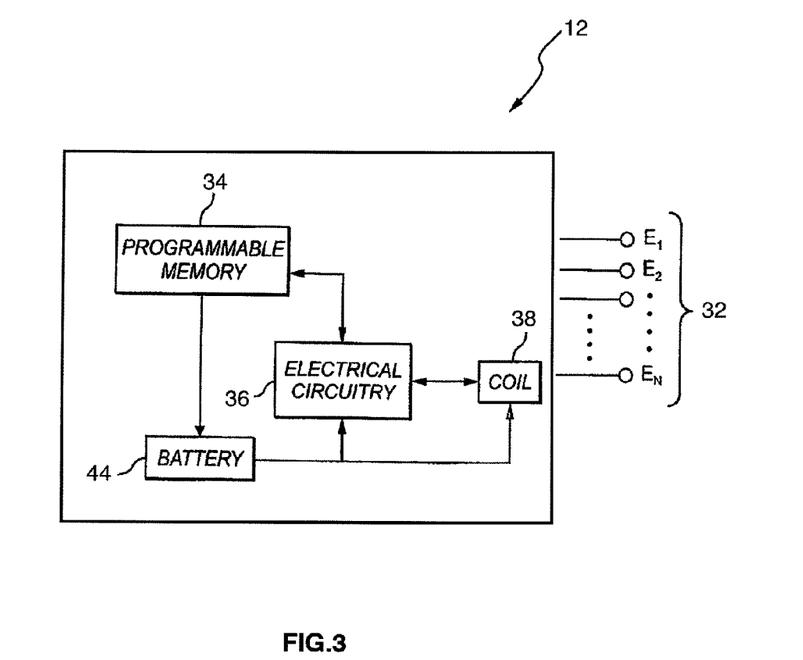
FIG. 3 is a block diagram of the internal components of the microstimulator of FIG. 2.

Turning to FIGS. 2 and 3, the microstimulator 12 is designed to stimulate tissue that is local to its implantation site. Preferably, the microstimulator 12 is small enough to be implanted almost anywhere in the human body for treatment of a wide variety of diseases and disorders. For example, the microstimulator 12 may have a length l in the range of 26-30 mm, a width w in the range of 6.5-8 mm, and a thickness t in the range of 3.5-5 mm. The microstimulator 12 is generally rectangular, although it should be understood that the microstimulator 12 may alternatively be cylindrical, elongated oval, square, or any other suitable shape.

To this end, the microstimulator 12 comprises a circuit module 26, an energy storage module 28, a feed-through module 30, and a plurality of exterior surface electrodes 32. The energy storage module 28 is coupled on one end to the circuit module 26 and on the other end to the feed-through module 30.

The circuit module 26 includes an interior cavity that houses a programmable memory 34, active electrical circuitry 36, and telemetry/charging coil 38. The active electrical circuitry 36 within the circuit module 26 is coupled to the electrodes 32 via a number of feed-throughs 40 in the feed-through assembly 30 and a plurality of respective electrical traces 42. Any other components of the microstimulator 12 that may best serve a particular application may also be housed within the circuit module 26.

The energy storage module 28 contains an energy storage device 44, such as a battery, is configured to output a voltage used to supply the various components within the microstimulator 12 with power. The battery 44 also provides power for any stimulation current applied by the microstimulator 12 to a stimulation site. The battery 44 may be a primary battery, a rechargeable battery, a capacitor, or any other suitable power source.

The electrodes 32 (labeled $E_1$-$E_N$) are configured to apply the electrical pulsed stimulation current to the stimulation site. As depicted in FIG. 3, there may be any number of electrodes 32 as best serves a particular application. In some examples, one or more of the electrodes 32 may be designated as stimulating electrodes and one of the electrodes 32 may be designated as an indifferent electrode used to complete one or more stimulation circuits. Any of the electrodes 32 may be configured as anodes or cathodes and the polarity of each electrode 32 may be reprogrammed. In an alternative embodiment, an electrode carrying lead (not shown) may be coupled to the microstimulator 12 in addition to or as an alternative to the electrodes 32.

The programmable memory 34 is used for storing one or more sets of data, for example, electrical stimulation parameters. The programmable memory 34 allows a patient, clinician, or other user of the microstimulator 12 to adjust the electrical stimulation parameters to levels that are safe and efficacious for a particular medical condition and/or for a particular patient. The electrical stimulation parameters may control various parameters of the stimulation current applied to the stimulation site including, but not limited to, electrode polarity, pulse amplitude, pulse rate, pulse width, burst pattern (e.g., burst on time and burst off time), duty cycle or burst repeat interval, ramp on time and ramp off time of the pulsed stimulation current that is applied to the stimulation site. The programmable memory 34 may be any type of memory unit such as, but not limited to, random access memory (RAM), static RAM (SRAM), a hard drive, or the like.

The active electrical circuitry 36 is configured for generating pulsed electrical stimulation current that is delivered to the stimulation site via the electrodes 32. The electrical circuitry 36 may be configured to produce monopolar or multipolar stimulation. The electrical circuitry 36 may include one or more processors (not shown) configured for decoding stimulation parameter information stored in the programmable memory 34 and generating the corresponding pulsed electrical stimulation current. In some embodiments, the microstimulator 12 has at least four channels and drives up to sixteen electrodes or more. The active electrical circuitry 36 may include additional circuitry such as capacitors, integrated circuits, resistors, coils, and the like configured to perform a variety of functions as best serves a particular application.

The telemetry/charging coil 38 is configured for transcutaneously receiving data from and/or transmitting data to an external control device, such as the RC 14 or CP 16, and receiving power from the external charger 18 that is stored in the battery 40. In the illustrated embodiment, such data and power is transmitted and/or received via electromagnetic energy (also referred to as a radio frequency (RF) field).

Further details discussing microstimulators are disclosed in U.S. patent application Ser. No. 10/178,011, entitled "Implantable Microstimulators with Programmable Multielectrode Configuration and Uses Thereof," and U.S. patent application Ser. No. 11/280,620, entitled "Implantable Stimulator," which are expressly incorporated herein by reference. In alternative embodiments, an implantable pulse generator (IPG) with one or more attached neurostimulation lead (not shown) may be used in place of the microstimulator, as disclosed in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than a microstimulator or IPG, the neurostimulation system 10 may alternatively utilize a neurostimulator in the form of an implantable receiver-stimulator (not shown). In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
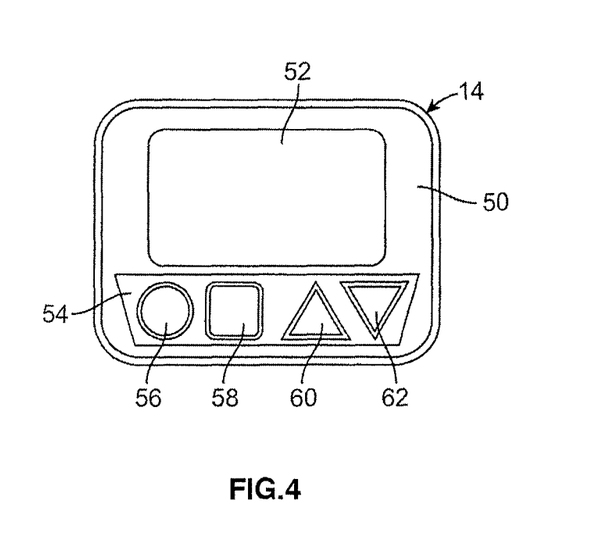
FIG. 4 is a plan view of a remote control that can be used in the peripheral tissue stimulation system of FIG. 1.

Referring now to FIG. 4, one exemplary embodiment of an RC 14 will now be described. As previously discussed, the RC 14 is capable of communicating with the microstimulator 12 or CP 16. The RC 14 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the microstimulator 12 to be turned ON and OFF, provide for the adjustment or setting of stimulation parameters within the microstimulator 12, and provide for selection between screens.

In the illustrated embodiment, the button 56 serves as an ON/OFF button that can be actuated to turn the microstimulator 12 ON and OFF. The button 58 serves as a select button that allows the RC 14 to switch between screen displays and/or parameters. The buttons 60 and 62 serve as up/down buttons that can be actuated to increment or decrement any of stimulation parameters of the pulse generated by the microstimulator 12, including pulse amplitude, pulse width, and pulse rate. For example, the selection button 58 can be actuated to place the RC 14 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 14 are disclosed in U.S. Pat. No. 6,895,280, which has previously been incorporated herein by reference.

Figure 5:
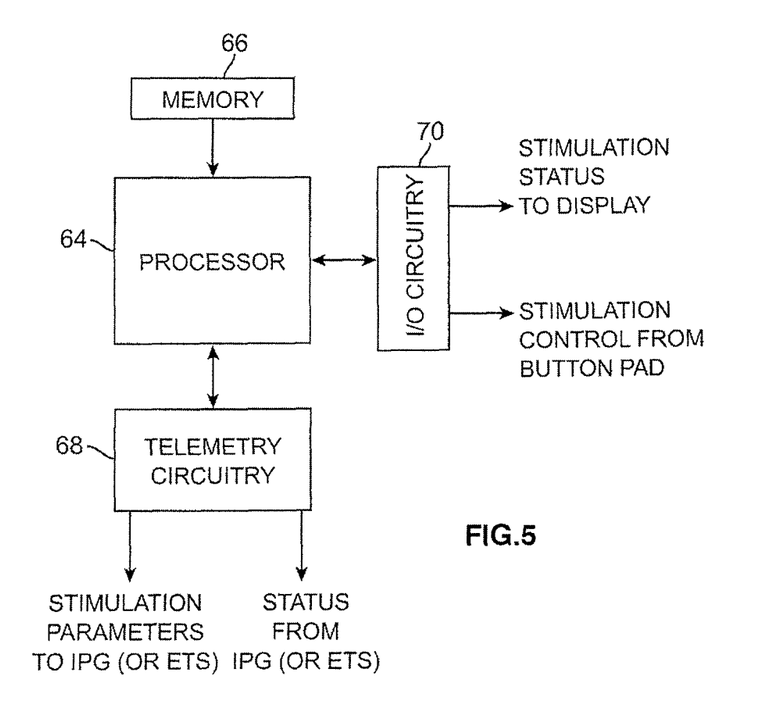
FIG. 5 is a block diagram of the internal componentry of the remote control of FIG. 4.

Referring to FIG. 5, the internal components of an exemplary RC 14 will now be described. The RC 14 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the microstimulator 12 and receiving status information from the microstimulator 12, and input/output circuitry 70 for receiving stimulation control signals from the button pad 54 and transmitting status information to the display screen 52 (shown in FIG. 4). As well as controlling other functions of the RC 14, which will not be described herein for purposes of brevity, the processor 64 generates new stimulation parameter sets in response to the user operation of the button pad 54. These new stimulation parameter sets would then be transmitted to the microstimulator 12 via the telemetry circuitry 68. Further details of the functionality and internal componentry of the RC 14 are disclosed in U.S. Pat. No. 6,895,280, which has previously been incorporated herein by reference.

As briefly discussed above, the CP 16 greatly simplifies the programming of multiple electrode combinations, allowing the user (e.g., the physician or clinician) to readily determine the desired stimulation parameters to be programmed into the microstimulator 12, as well as the RC 14. Thus, modification of the stimulation parameters in the programmable memory of the microstimulator 12 after implantation is performed by a user using the CP 16, which can directly communicate with the microstimulator 12 or indirectly communicate with the microstimulator 12 via the RC 14.

As shown in FIG. 2, the overall appearance of the CP 16 is that of a laptop personal computer (PC), and in fact, may be implanted using a PC that has been appropriately configured to include a directional-programming device and programmed to perform the functions described herein. Thus, the programming methodologies can be performed by executing software instructions contained within the CP 16. Alternatively, such programming methodologies can be performed using firmware or hardware. In any event, the CP 16 may actively control the characteristics of the electrical stimulation generated by the microstimulator 12 to allow the optimum stimulation parameters to be determined based on patient feedback and for subsequently programming the microstimulator 12 with the optimum stimulation parameters.

To allow the user to perform these functions, the CP 16 includes a mouse 72, a keyboard 74, and a display screen 76 housed in a case 78. In the illustrated embodiment, the display screen 76 is a conventional screen. It is to be understood that in addition to, or in lieu of, the mouse 72, other directional programming devices may be used, such as a trackball, touchpad, or joystick, can be used. Alternatively, instead of being conventional, the display screen 76 may be a digitizer screen, such as touchscreen) (not shown), may be used in conjunction with an active or passive digitizer stylus/finger touch.

Figure 6:
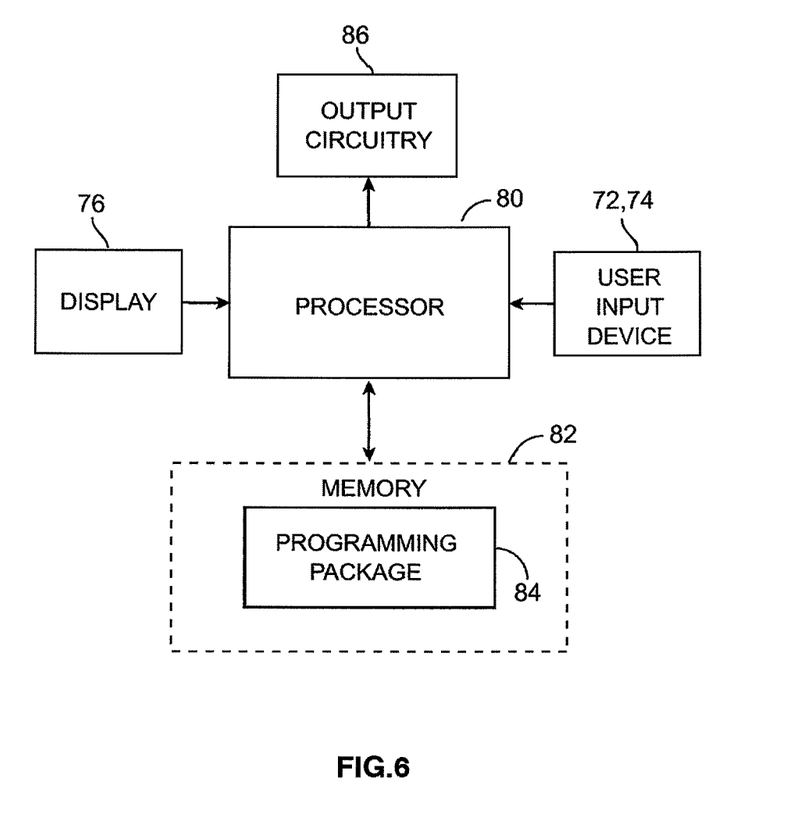
FIG. 6 is a block diagram of the components of a clinician programmer that can be used in the peripheral tissue stimulation system of FIG. 1.

As shown in FIG. 6, the CP 16 generally includes a processor 80 (e.g., a central processor unit (CPU)) and memory 82 that stores a stimulation programming package 84, which can be executed by the processor 80 to allow the user to program the microstimulator 12 and RC 14. The CP 16 further includes output circuitry 86 (e.g., via the telemetry circuitry of the RC 14) for downloading stimulation parameters to the microstimulator 12 and RC 14 and for uploading stimulation parameters already stored in the memory 66 of the RC 14, via the telemetry circuitry 68 of the RC 14.

Execution of the programming package 84 by the processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the microstimulator 12 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Figure 7:
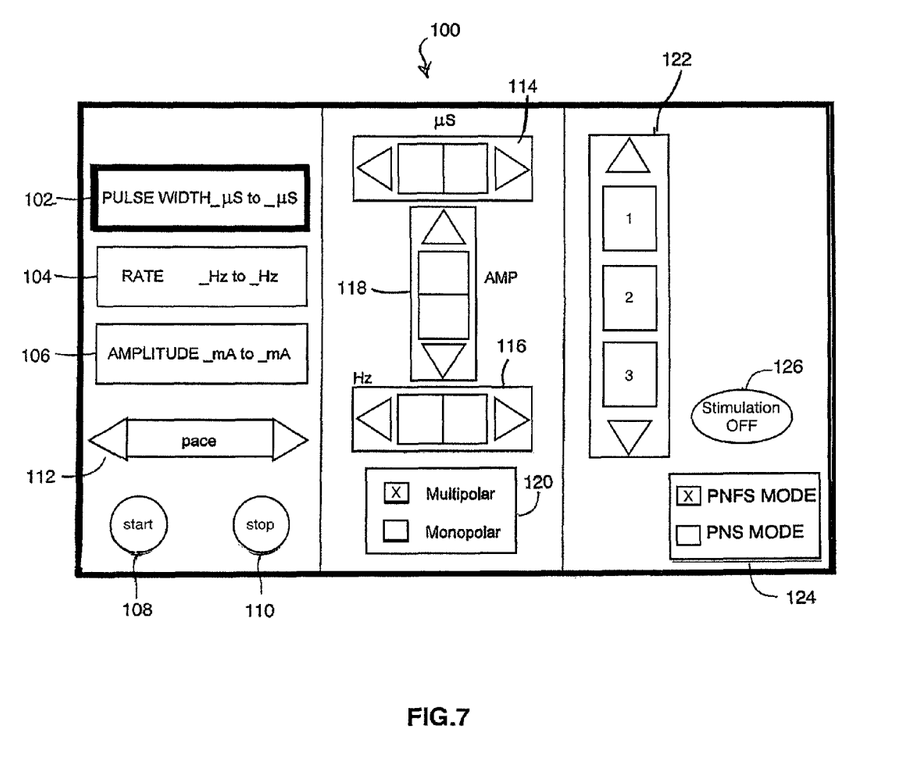
FIG. 7 is a plan view of a programming screen created by the clinician programmer of FIG. 6 for programming the microstimulator of FIG. 2.

An example of a programming screen 100 that can be generated by the CP 16 is shown in FIG. 7. The programming screen 100 allows a user to perform automated stimulation parameter testing, manual stimulation parameter testing, and electrode combination selection functions.

The programming screen 100 includes various stimulation parameter entries that define the ranges of stimulation parameters to be automatically tested. In particular, the programming screen includes a pulse width entry 102 (expressed in microseconds (µs)), a pulse rate entry 104 (expressed in Hertz (Hz)), and a pulse amplitude entry 106 (expressed in milliamperes (mA)). The user may enter a "begin" value and an "end" value for each stimulation parameter to be automatically adjusted. In one embodiment, only a single parameter (e.g., pulse width entry 102) is highlighted to be auto-adjusted. The programming screen 100 also includes a start button 108, which begins the automatic adjustment of the highlighted stimulation parameter from its "begin" value through a minimum increment to its "end" value, and a stop button 100, which halts the automatic adjustment of the highlighted stimulation parameter. The programming screen 100 also includes a pacing control 112, the left arrow of which can be clicked to decrease the speed of the parameter adjustment and the right arrow of which can be clicked to increase the speed of the parameter adjustment.

The programming screen 100 also includes various stimulation parameter controls that can be operated by the user to manually adjust stimulation parameters. In particular, the programming screen 100 includes a pulse width adjustment control 114 (expressed in microseconds (µs)), a pulse rate adjustment control 116 (expressed in Hertz (Hz)), and a pulse amplitude adjustment control 118 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 120, which includes check boxes that can be alternately clicked by the user to provide multipolar or monopolar stimulation.

The programming screen 100 also includes an electrode combination control 122 having arrows that can be clicked by the user to select one of three different electrode combinations 1-3. Each of the electrode combinations 1-3 can be conventionally created either manually; for example, clicking on selected electrodes of a graphical electrode array (not shown) as anodes and cathodes and defining a percentage anodic current or cathodic current for each selected electrode (e.g., turning off electrode E1 as an anode, and turning on electrode E2 as an anode, and defining an anodic current for electrode E2), or automatically; for example, by gradually shifting current between anodic ones of the electrodes and/or gradually shifting current between cathodic ones of the electrodes via a directional device, such as a joystick or mouse (e.g., shifting anodic electrical current from electrode E1 to electrode E2 in 5% increments).

The programming screen 100 also includes a peripheral stimulation selection control 124, which includes check boxes that can be alternately clicked by the user to selectively place the system 10 between a PNFS mode, in which the microstimulator 12 can be operated or programmed to perform only PNFS, and a PNS mode, in which the microstimulator 12 can be operated or programmed to perform only PNS. In the illustrated embodiment, the peripheral stimulation selection control 124 is implemented as a graphical icon that can be clicked with a mouse or touched with a finger in the case of a touchscreen. Alternatively, the peripheral stimulation selection control 124 may be incorporated into the programming interface device as a button or key that is pressed when activated and then depressed when released, such as an Alt key. Any control mechanism that programs the microstimulator 12 to operate in either of the PNFS and PNS modes in response to a single actuation can be utilized as the peripheral stimulation selection control 124. The programming screen 100 further comprises a stimulation on/off control 126 that can be alternately clicked to turn the stimulation on or off.

Significantly, the microstimulator 12 can be operated or programmed to perform PNFS or PNS by adjusting the pulse width and polarity of the pulsed stimulation current output by the microstimulator 12. Notably, it has been discovered that by selecting the pulse width and polarity of pulsed electrical current applied to a peripheral region, local nerve endings (the stimulation of which is associated with PNFS) and neural axons (the stimulation of which is associated with PNS) can be selectively activated.

In particular, an experiment was performed on five subjects during which a stimulation electrode was used to transcutaneously stimulate a peripheral region adjacent the ulnar nerve of the five subjects while the pulse width and polarity of the stimulation current were adjusted. Notably, it is expected that the therapeutic effects of transcutaneous stimulation are similar to those of subcutaneous stimulation, and thus, the experimental results of the transcutaneous stimulation may be applied to support conclusions involving subcutaneous stimulation.

During stimulation, the pulse width of the stimulation current was set at 50 μs, 100 μs, 200 μs, 500 μs, 700 μs, and 1000 μs for each of a cathodic stimulation current and an anodic stimulation current, and each subject was requested to provide feedback for each setting as to whether a local sensation (resulting from the stimulation of nerve endings in the elbow), which was defined as a sensation within 5 cm of the stimulation electrode, a remote sensation (resulting from the stimulation of the ulnar nerve), which was defined as a sensation within the hand, or both a local sensation and a remote sensation was experienced. For each pulse width setting, the amplitude of the current was increased from zero until the subject experienced a sensation from the stimulation. If a subject experienced only a local sensation or only a remote sensation, the local sensation or the remote sensation was quantified as 100%, and if the subject experienced both a local sensation and a remote sensation, each of the local and remote sensations was quantified as 50%. The data from the five subjects were then averaged.

Figure 8A:
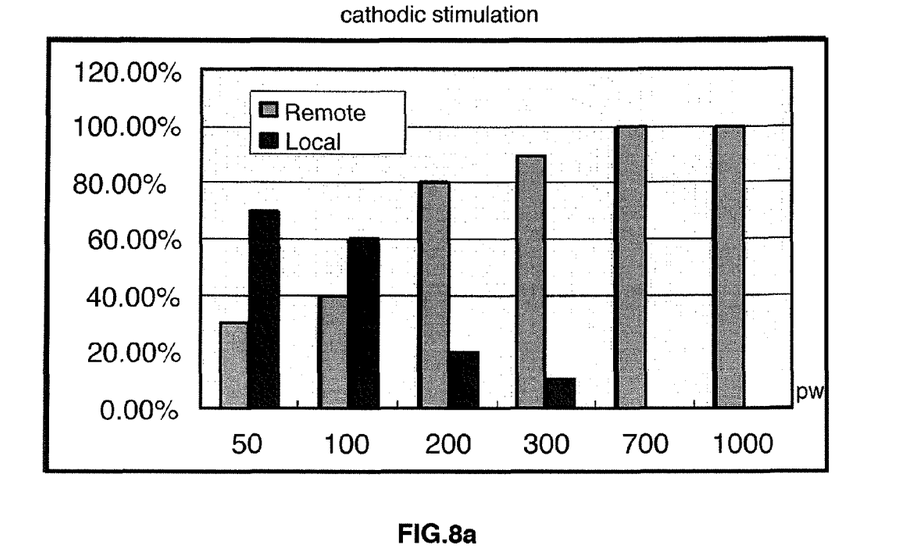
FIG. 8a is a bar graph illustrating the local and remote sensations experienced by five subjects in accordance with different pulse widths of applied cathodic electrical current.
Figure 9A:
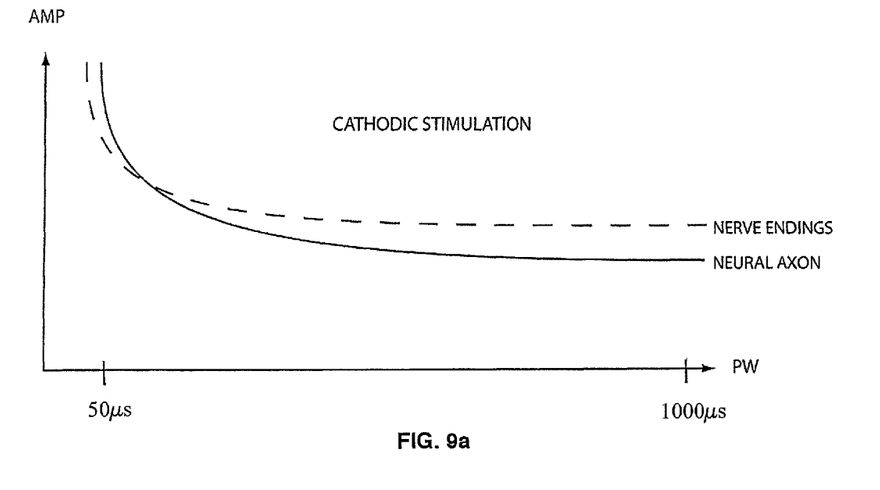

As can be seen from FIG. 8*a*, when cathodic electrical current was used to stimulate the subjects, a pulse width of 500 μs or less yielded a mixture of both a local sensation and a remote sensation, while a pulse width greater than 500 μs yielded only a remote sensation. The strength duration curves illustrated in FIG. 9*a*, which represent the pulse amplitude and pulse width needed to respectively stimulate nerve endings in the elbow region and the ulnar nerve, were generated from the cathodic electrical current stimulation experiment presented in FIG. 8*a*. As can be appreciated from a review of FIG. 9*a*, the separation of the strength duration curves for the respective nerve endings and ulnar nerve is relatively large at relatively high pulse widths. As such, selectively between activation of the nerve endings and the ulnar nerve is relatively high at these relatively high pulse durations for cathodic current stimulation. Furthermore, the strength duration curve for the ulnar nerve has a lower threshold than that of the nerve endings at relatively high pulse widths, and as such, the ulnar nerve will be stimulated before the nerve endings.

Figure 8B:
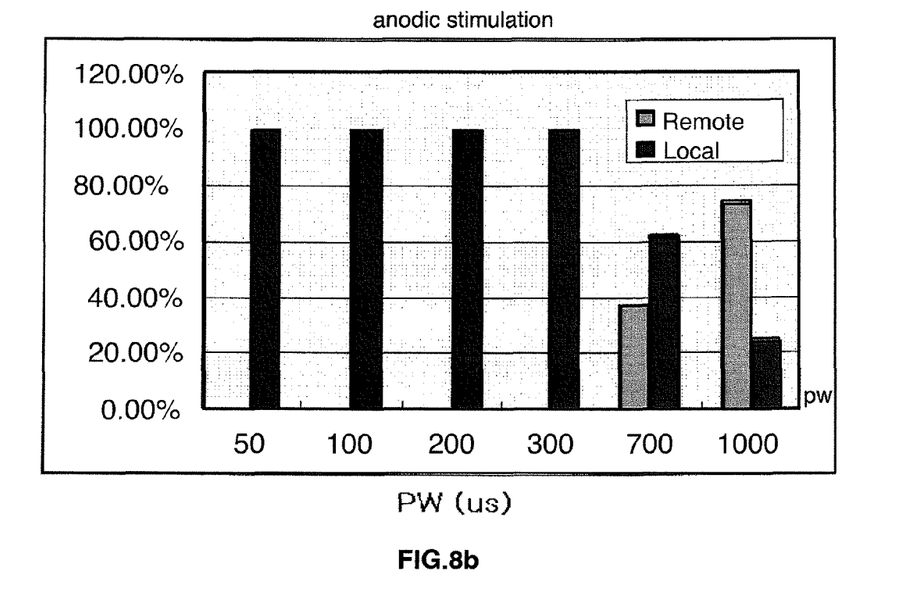
FIG. 8b is a bar graph illustrating the local and remote sensations experienced by five subjects in accordance with different pulse widths of applied anodic electrical current.
Figure 9B:
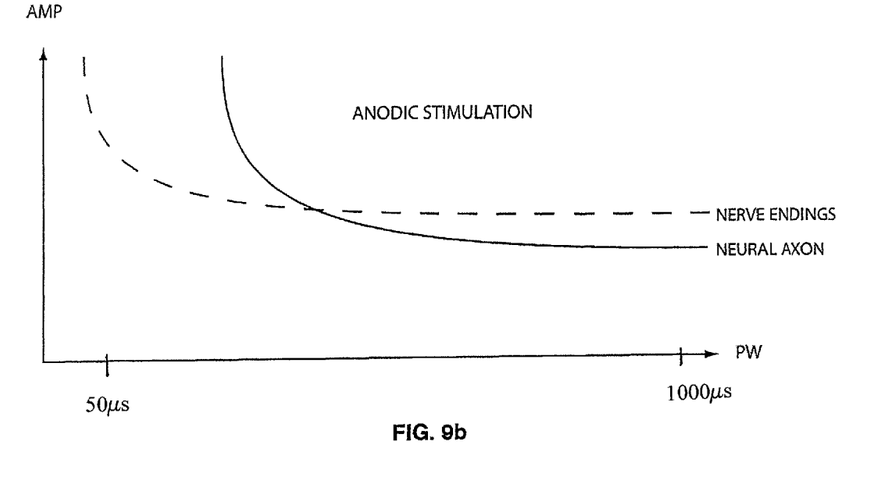
FIG. 9b is a diagram of strength-duration curves for the stimulation of nerve endings and neural axons generated from the bar graph of FIG. 8b.

In contrast, as can be seen from FIG. 8*b*, when anodic electrical current was used to stimulate the subjects, a pulse width of 700 μs or greater yielded a mixture of both a local sensation and a remote sensation, while a pulse width less than 700 μs yielded only a local sensation. The strength duration curves illustrated in FIG. 9*b*, which represent the pulse amplitude and pulse width needed to respectively stimulate nerve endings in the elbow region and the ulnar nerve were generated from the anodic electrical current stimulation experiment presented in FIG. 8*b*. As can be appreciated from a review of FIG. 9*b*, the separation of the strength duration curves for the respective nerve endings and ulnar nerve is relatively large at relatively low pulse durations. As such, selectively between activation of the nerve endings and ulnar nerve is relatively low at these relatively high pulse durations for anodic current stimulation. Furthermore, the strength duration curve for the nerve endings has a lower threshold than that of the ulnar nerve at relatively low pulse widths, and as such, the nerve endings will be stimulated before the ulnar nerve.

Thus, from this, it can be gathered that polarity and pulse width of an applied electrical stimulation current are critical parameters in selectively activating local nerve endings and neural axons for the purposes of selectively performing PNFS and PNS.

To this end, when the microstimulator 12 is programmed by the CP 16 to operate in the PNFS mode (i.e., by clicking the check box associated with the PNFS mode on the peripheral stimulation selection control 124), the microstimulator 12 may convey anodic electrical current through the selected stimulation electrode or electrodes at a pulse width less than a certain value (e.g., less than 700 μs). This can be accomplished by only permitting the user to select certain electrodes as anodes and programming the microstimulator 12 within a relatively low pulse width range (e.g., using an upper limit value less than 700 μs) using the pulse width entry 102 or pulse width adjustment control 114. Alternatively, the CP 16 may automatically program the microstimulator 12 to convey anodic stimulation current at a low pulse width.

In contrast, when the microstimulator 12 is programmed to operate in the PNS mode (i.e., by clicking the check box associated with the PNS mode on the peripheral stimulation selection control 124), the microstimulator 12 is programmed, such that cathodic electrical current is conveyed through the selected stimulation electrode or electrodes at a pulse width greater than a certain value (e.g., greater than 500 μs). This can be accomplished by only permitting the user to select certain electrodes as cathodes and programming the microstimulator 12 within a relatively high pulse width range (e.g., using an lower limit value greater than 500 μs) using the pulse width entry 102 or pulse width adjustment control 114. Alternatively, the CP 16 may automatically program the microstimulator 12 to convey cathodic stimulation current at a high pulse width.

PNFS and PNS can not only be selectively performed my placing the system 10 in the PNFS programming mode or PNS programming mode via actuation of the peripheral stimulation selection control 124, but can also be selectively performed manually.

In particular, referring back to FIG. 1, if only PNFS is desired (in this case, by stimulation of the nerve endings 47), anodic pulsed electrical current is initially conveyed at a particular pulse width into the peripheral region 45 of the patient and the pulse amplitude is increased until either a therapeutic effect, side effect, or both is created. Preferably, the pulse width is low enough (e.g., lower than 700 μs), such that the initial conveyance of the anodic pulsed electrical current results in only PNFS (in effect, creating a therapeutic effect (e.g., reduction or elimination of pain) local to the peripheral tissue region 45 without creating a side effect remote from the peripheral tissue region 45). Because the optimum pulse width may not be known yet, it is possible that the initial conveyance of the anodic pulsed electrical current may inadvertently result in PNS (in this case, by stimulation of the neural axon 48) in addition to the desired PNFS (in effect, creating an undesirable side effect remote from the peripheral tissue region 45). In this case, anodic pulsed electrical current is subsequently conveyed into the peripheral region 45 of the patient, and while maintaining the pulse amplitude, the pulse width is decreased until only PNFS is performed.

If only PNS is desired (in this case, by stimulation of the neural axon 48), cathodic pulsed electrical current is initially conveyed at a particular pulse width into the peripheral region 45 of the patient and the pulse amplitude is increased until either a therapeutic effect, side effect, or both is created. Preferably, the pulse width is high enough (e.g., greater than 500 μs), such that the initial conveyance of the cathodic pulsed electrical current results in only PNS (in effect, creating a therapeutic effect (e.g., reduction or elimination of pain) remote from the peripheral tissue region 45 without creating a side effect local to the peripheral tissue region 45). Because the optimum pulse width may not be known yet, it is possible that the initial conveyance of the cathodic pulsed electrical current may inadvertently result in PNFS (in this case, by stimulation of the nerve endings 47) in addition to the desired PNS (in effect, creating an undesirable side effect local to the peripheral neural tissue region 45). In this case, cathodic pulsed electrical current is subsequently conveyed into the peripheral region 45 of the patient, and while maintaining the pulse amplitude, the pulse width is increased until only PNS is performed.

Although the foregoing techniques have been described as being implemented in the CP 16, it should be noted that this technique may be alternatively or additionally implemented in the RC 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation control system for use with a neurostimulator, comprising:
    a user interface configured for receiving an input from a user, the user interface having a peripheral stimulation selection control; and
    a controller configured for, in response to a single actuation of the peripheral stimulation selection control, operating the neurostimulation control system in a dedicated peripheral nerve field stimulation (PNFS) programming mode that only allows the user to program the neurostimulator to convey pulsed anodic stimulation current at a pulse width below an upper limit, and for, in response to another single actuation of the peripheral stimulation selection control, operating the neurostimulation control system in a dedicated peripheral nerve stimulation (PNS) programming mode that only allows the user to program the neurostimulator to convey pulsed cathodic stimulation current at a pulse width above a lower limit.

2. The neurostimulation control system of claim 1, wherein the upper limit is less than 700 μs.

3. The neurostimulation control system of claim 1, wherein the lower limit is greater than 500 μs.

4. The neurostimulation control system of claim 1, wherein the peripheral stimulation selection control comprises at least one graphical icon.

5. The neurostimulation control system of claim 1, wherein the user interface and controller are contained within an external control device.

6. A neurostimulation control system for use with a neurostimulator, comprising:
    a user interface configured for receiving an input from a user, the user interface having a peripheral stimulation selection control; and
    a controller configured for, in response to a single actuation of the peripheral stimulation selection control, operating the neurostimulation control system in a PNFS programming mode that automatically programs the neurostimulator to convey pulsed anodic stimulation current at a first pulse width, and for, in response to another single actuation of the peripheral stimulation selection control, operating the neurostimulation control system in a PNS programming mode that automatically programs the neurostimulation to convey pulsed cathodic stimulation current at a second pulse width.

7. The neurostimulation control system of claim 6, wherein the first pulse width is less than 700 μs.

8. The neurostimulation control system of claim 6, wherein the second pulse width is greater than 500 μs.

9. A neurostimulation control system for use with a neurostimulator, comprising:
- a user interface configured for receiving an input from a user; and
- a controller configured for, in response to the user input, selectively operating the neurostimulation control system between a first programming mode that only allows the user to program the neurostimulator to convey pulsed anodic stimulation current at a pulse width below an upper limit, and a second programming mode that only allows the user to program the neurostimulator to convey pulsed cathodic stimulation current at a pulse width above a lower limit.

10. The neurostimulation control system of claim 9, wherein the upper limit is less than 700 μs.

11. The neurostimulation control system of claim 9, wherein the lower limit is greater than 500 μs.

12. The neurostimulation control system of claim 9, wherein the peripheral stimulation selection control comprises at least one graphical icon.

13. The neurostimulation control system of claim 9, wherein the user interface and controller are contained within an external control device.

14. The neurostimulation control system of claim 9, wherein the user interface comprises a control mechanism, and wherein the controller is configured for selectively operating the neurostimulation control system between the first programming mode and the second programming mode in response to a single actuation of the control mechanism.

15. A neurostimulation control system for use with a neurostimulator, comprising:
- a user interface configured for receiving an input from a user; and
- a controller configured for, in response to the user input, selectively operating the neurostimulation control system between a first programming mode that automatically programs the neurostimulator to convey pulsed anodic stimulation current at a first pulse width, and a second programming mode that automatically programs the neurostimulation to convey pulsed cathodic stimulation current at a second pulse width.

16. The neurostimulation control system of claim 15, wherein the first pulse width is less than 700 μs.

17. The neurostimulation control system of claim 15, wherein the second pulse width is greater than 500 μs.

18. The neurostimulation control system of claim 15, wherein the peripheral stimulation selection control comprises at least one graphical icon.

19. The neurostimulation control system of claim 15, wherein the user interface and controller are contained within an external control device.

20. The neurostimulation control system of claim 15, wherein the user interface comprises a control mechanism, and wherein the controller is configured for selectively operating the neurostimulation control system between the first programming mode and the second programming mode in response to a single actuation of the control mechanism.

* * * * *